United States Patent [19]

Bugay

[11] 4,112,491
[45] Sep. 5, 1978

[54] DIRECT READOUT REAL TIME PHYSIOLOGICAL PARAMETER ANALOG COMPUTER

[75] Inventor: Al Bugay, Canaan, N.H.

[73] Assignee: Life Sciences, Inc., Greenwich, Conn.

[21] Appl. No.: 812,752

[22] Filed: Jul. 5, 1977

[51] Int. Cl.$^2$ .......................... A61B 5/04; G06F 15/20
[52] U.S. Cl. ................................. 364/415; 128/2.05 F; 128/2.1 R; 235/92 FL; 364/571
[58] Field of Search ............................... 364/415–417, 364/800, 807, 510, 571; 128/2.05 R, 2.05 C, 2.05 F, 2.1 R; 73/194 R; 235/92 FL

[56] References Cited

U.S. PATENT DOCUMENTS

| | | | |
|---|---|---|---|
| 3,796,213 | 3/1974 | Stephens | 128/2.05 R |
| 3,811,040 | 5/1974 | Weinfurt et al. | 364/415 |
| 3,994,284 | 11/1976 | Voelker | 364/416 |

Primary Examiner—Malcolm A. Morrison
Assistant Examiner—Errol A. Krass
Attorney, Agent, or Firm—Charles E. Temko

[57] ABSTRACT

A medical electronic diagnostic device particularly suitable for determining and displaying segmental pulsatile flow of a patient. Means are provided for stabilization of a calibrated segmental volume time curve relative to a baseline, so as to eliminate the effect of patient movement during testing, as well as miscellaneous electrical noise. The disclosed device is capable, in addition to displaying a pulse volume curve, of measuring and recording the pulsatile component of the total blood flow.

3 Claims, 4 Drawing Figures

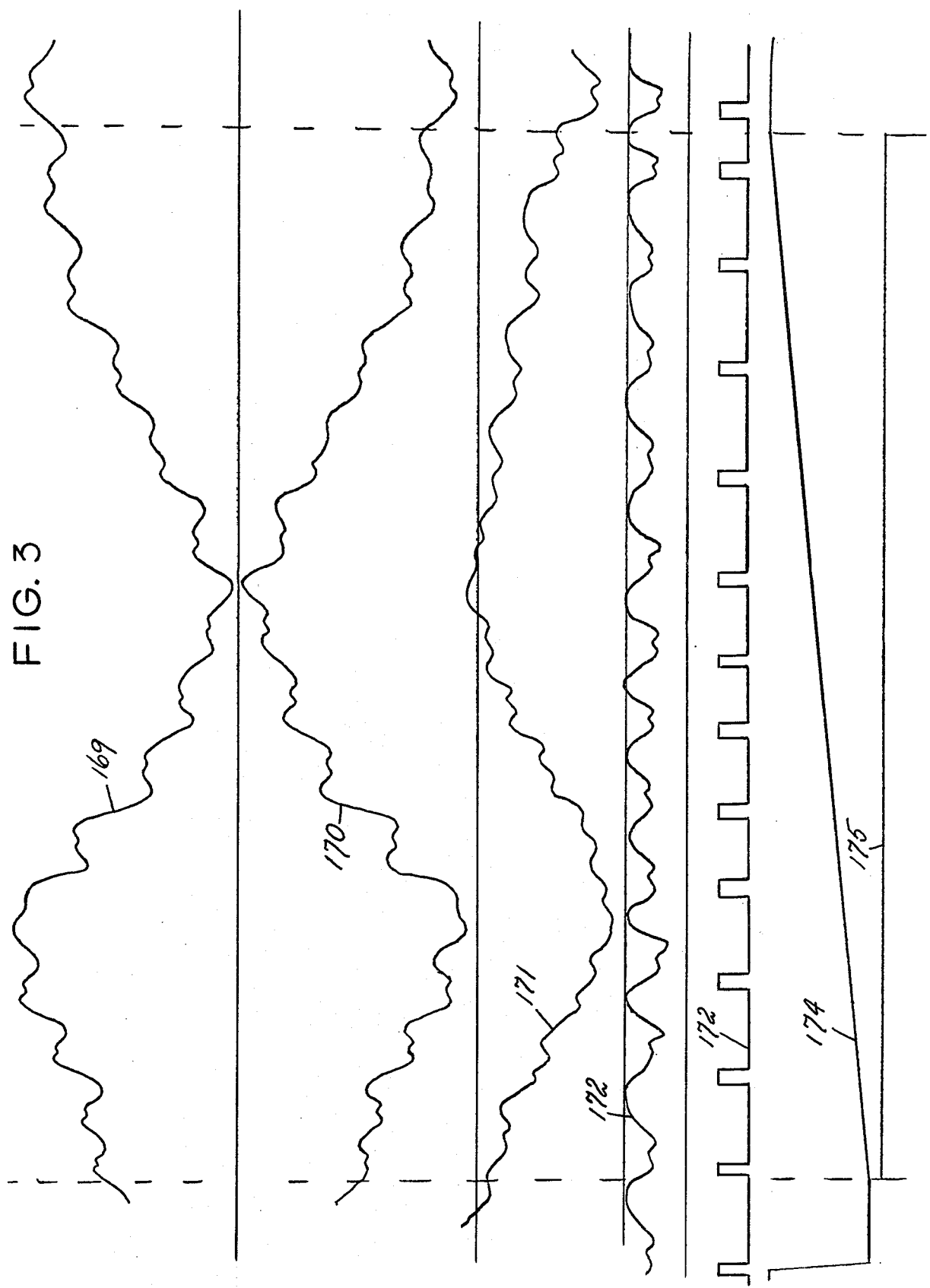

DIRECT READOUT REAL TIME PHYSIOLOGICAL PARAMETER ANALOG COMPUTER

BACKGROUND OF THE INVENTION

The geometry of flow trace is of significance in detecting early atherosclerotic changes, as is the assessment of perfusion levels. Since arterial compliance is relatively linear over a local pulse pressure range, the geometries of the pulse volume and pulse pressure contours are quite similar. In essence, however, the pulse volume recording is a segmental volume-time tracing. If one differentiates the volume-time curve, a calibrated flow-time curve is obtained, representing the pulsatile component of the total flow.

The known art includes well developed devices for obtaining the above information in displayed and recorded form. However, because the detection of pulses at various locations on the body of a patient is essentially mechanical, unexpected movement of the patient during periods of measurement can cause a shifting of the electrical baseline which forms the ordinate against which the obtained curve is plotted. Miscellaneous electrical noise can have the same effect, although normally to a lesser degree. Prior art devices have failed to incorporate means for compensating against baseline shift, and as a result have produced output signals which are difficult to evaluate.

SUMMARY OF THE INVENTION

Briefly stated, the invention contemplates the provision of improved electrical circuitry in a device of the class described. In order to reduce a set of complex dynamic variables contained in a pulsatile heart beat wave form into a single meaningful output display, a real time analog computer utilizing novel analog processing circuits implemented with microelectric components is provided. Amplification factor, frequency selection, artificial baseline generation, time correlated signal summation, algebraic electronic addition, subtraction, multiplication, and division are all dynamic variables applied to the original signal in order to derive the final display value representing the volumetric analysis. Means are also provided for the elimination of spurious signals caused by major drift and body movement frequency components.

BRIEF DESCRIPTION OF THE DRAWINGS

In the drawings, to which reference will be made in the specification, similar reference characters have been employed to designate corresponding parts throughout the several views.

FIG. 3 is a graphic representation of the processing of wave forms generated during operation of the embodiment.

DETAILED DESCRIPTION OF THE DISCLOSED EMBODIMENT

Figure 1:
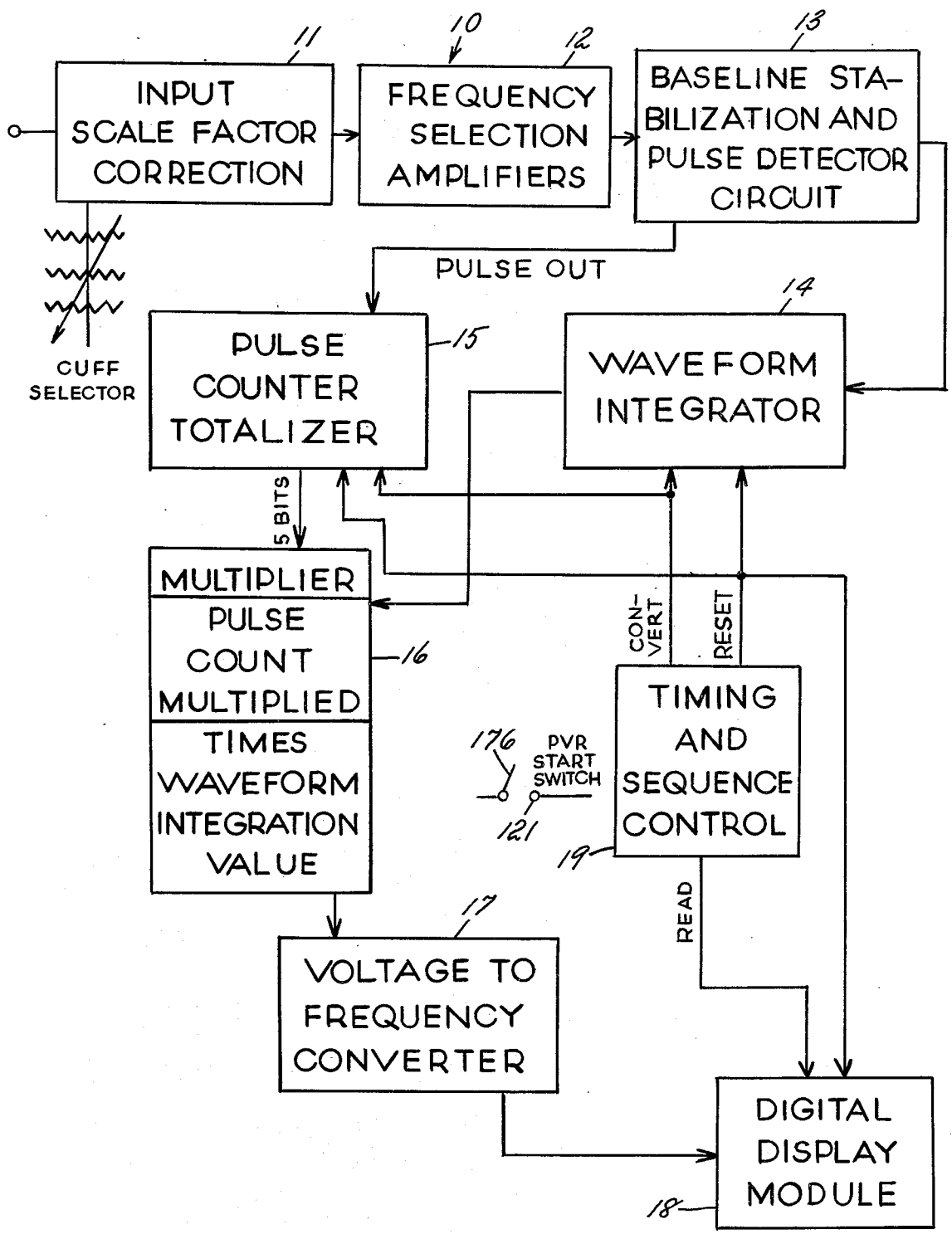
FIG. 1 is a block diagram showing the major electronic components comprising an embodiment of the invention.

In accordance with the invention, the device, generally indicated by reference character 10, (FIG. 1), comprises broadly: an input scale factor correction circuit 11, a frequency selection amplifier circuit 12, a baseline stabilization and pulse detector circuit 13, a wave form integrator circuit 14, a pulse counter circuit 15, a multiplier circuit 16, a voltage to frequency convertor circuit 17, a digital display module 18 and a timing and sequence control circuitry 19.

Figure 2A:
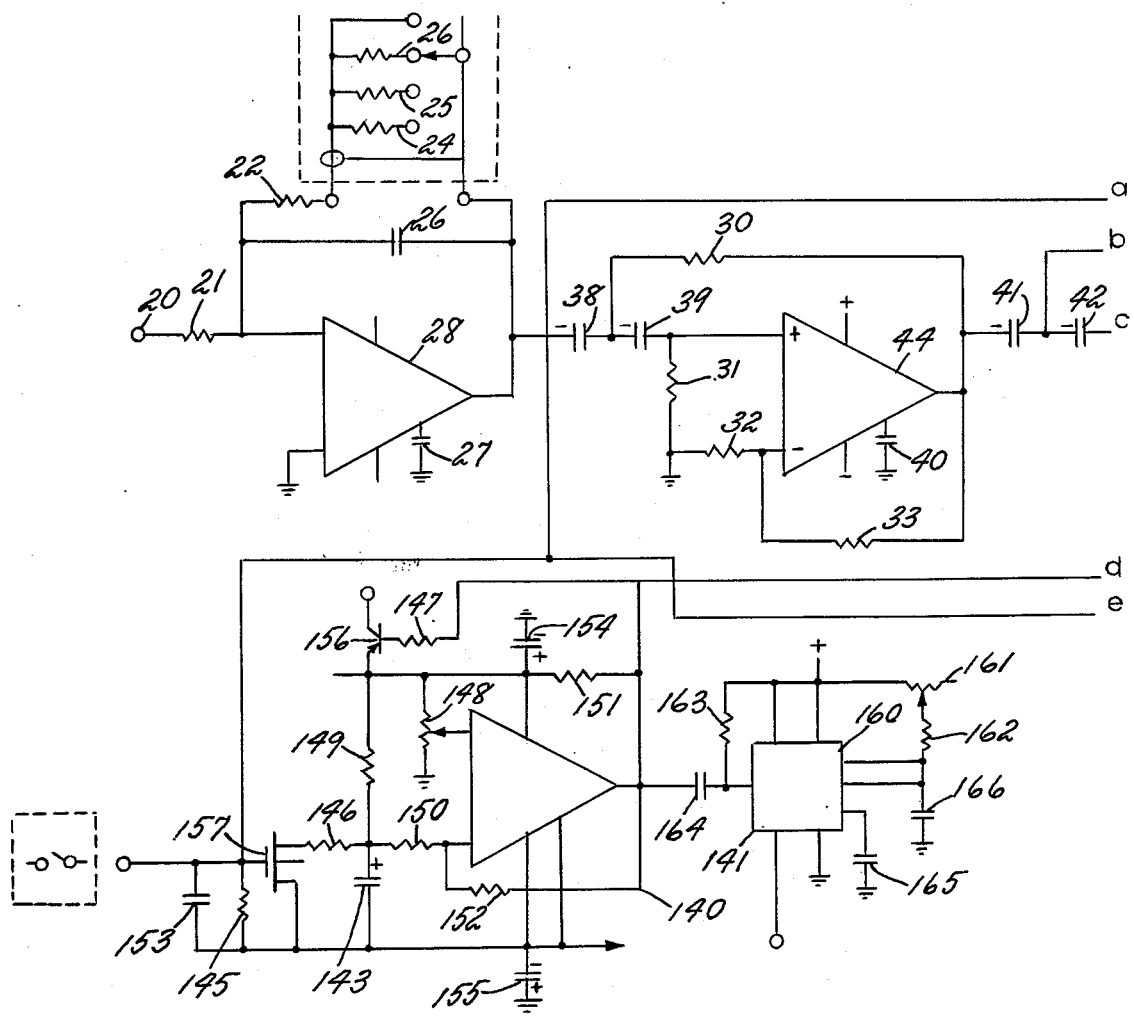
FIGS. 2a and 2b constitute a schematic wiring diagram showing in detail the components shown in FIG. 1.
Figure 2B:
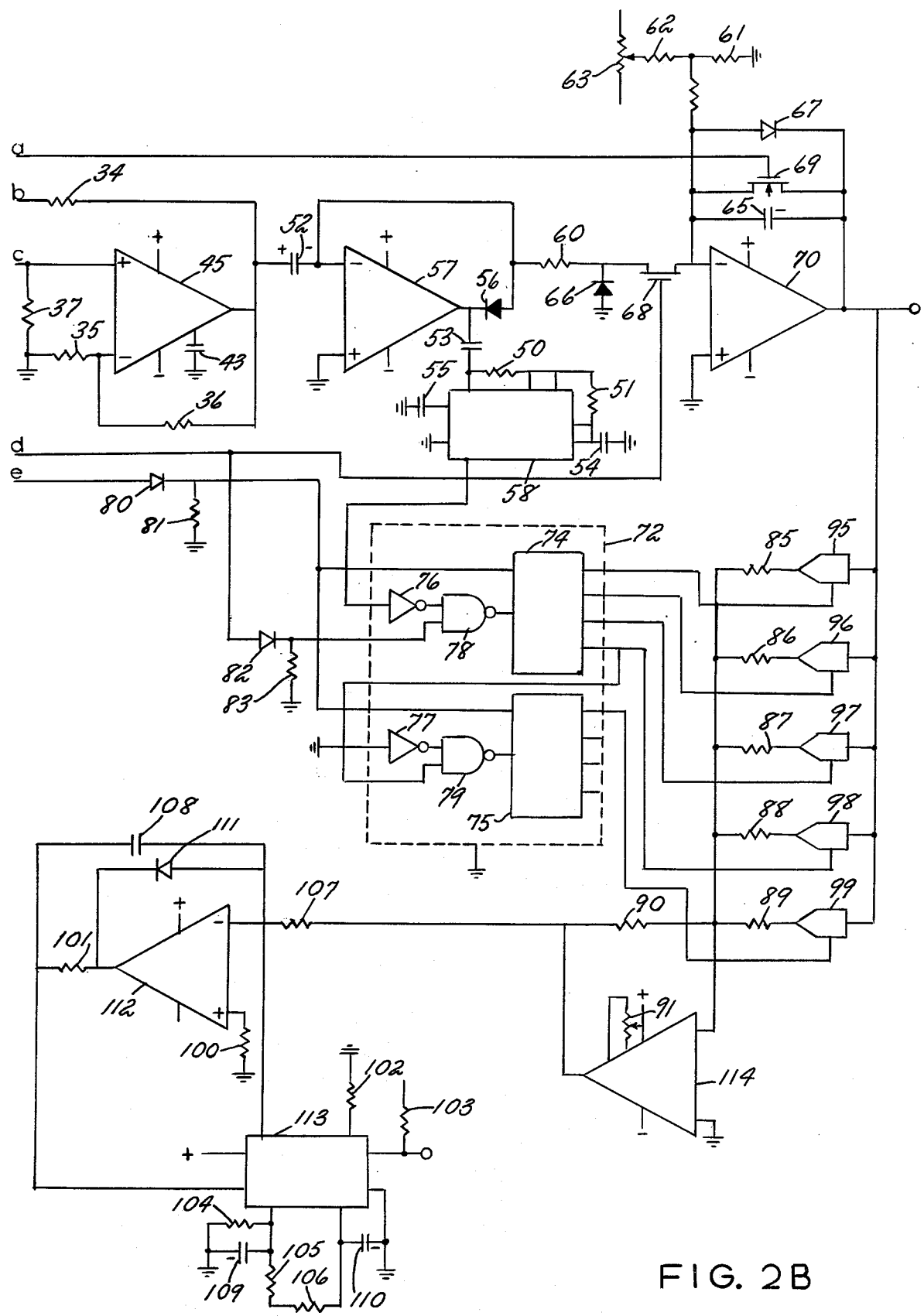

The input scale factor correction circuit 11 (FIG. 2) consists of an input terminal 20, resistors 21, 22, 23, 24 and 25; capacitors 26 and 27 and an integrated circuit 28. The component interconnection forms a negative feedback, variable gain, inverting operational amplifier circuit.

The frequency selection amplifier circuit includes resistors 30, 31, 32, 33, 34, 35, 36 and 37; and capacitors 38, 39, 40, 41, 42 and 43; as well as integrated circuits 44 and 45. This circuitry forms a four pole positive feedback active low pass filter.

The baseline stabilization and pulse detector circuit 13 includes resistors 50 and 51; capacitors 52, 53, 54 and 55; diode 56 and integrated circuits 57 and 58. This circuit removes floating baseline variations while at the same time it produces a simultaneous output signal which represents the basic cyclic fundamental input frequency to the circuit.

The circuit 13 operates in the following manner. The filtered pulsatile wave form appears reversed top from bottom at the plus(+) side of the input capacitor 52. The reversed top from bottom signal is a result of the inversion which has previously taken place in the circuit 11. The dynamic variations of the pulsatile flow wave form are coupled through capacitor 52. The direct current component of the wave form will be dependent upon the output of integrated circuit 57 through diode 56. Since the pulsatile flow wave form is inverted, it is required that all signal values be negative which indicate increasing amounts of pulsatile flow and lesser amounts of pulsatile flow to bring the wave form to 0 volts. Integrated circuit 57 is a microcircuit operational amplifier with an inverting (pin 2), and a non-inverting input (pin 3). The output appears on pin 6. The amplifier has approximately infinite gain (very large). The non-inverting side of the amplifier is grounded, and the signal of interest is applied to the inverting input at pin 2. As long as the absolute value of the inverted pulsatile flow wave form is negative, the output at pin 6 will be saturated positive (approximately 12 volts). Diode 46 will block any positive current from charging capacitor 52. However, if the input voltage at pin 2 should drift to the positive side of 0 volts, active clamping action will take place. A transition from negative, through 0, to positive at pin 2 will cause the output of integrated circuit 57, pin 6 to move at maximum slew rate from its previously positive saturation voltage to negative saturation voltage. As the output moves from positive to negative in a fraction of a microsecond, diode 56 becomes negative at minus one half volt and commences to allow integrated circuit 57 to supply a charging current to capacitor 52. This current counteracts the positive charge on capacitor 52, thereby reasserting a slightly negative charge thereon. At this time, the amplifier senses a negative slide of 0 voltage at its inverting input, and sends its output back to the positive saturated output which is blocked by diode 56. It will be appreciated that the pulsatile flow wave form voltage value will always be between 0 volts and a negative voltage value.

Integrated circuit 58, along with capacitors 53 to 55, inclusive, and resistor 51 form a monostable multivibrator. This circuit produces one constant width output pulse for each short burst of voltage appearing at its input. The negative going output transition of circuit 57 (pin 6) is coupled through capacitor 53 to the input of integrated circuit 58 (pin 2) in order to initiate an output pulse from pin 3. Pin 2 receives an input pulse each time that clamping action takes place in the circuit 57. Clamping action takes place one or more times during each pulsatile flow impulse wave form cycle. Circuit 58 produces only one output pulse per pulsatile flow impulse wave form cycle. The monostable multi-vibrator circuit locks out additional inputs during its timing function, thereby eliminating multiple triggers from a single pulsatile flow wave form cycle. The analog signal output is presented to resistor 60. The digital signal output is available at pin 3 of circuit 58, and is used to supply a pulse counter in a following circuit stage.

The wave form integrator circuit 14 is comprised of resistors 60, 61, 62, 63 and 64; capacitor 65, diodes 66 and 67; transistors 68 and 69; and integrated circuit 70. Resistors 63, 62, 61 and 64 form a zero setting network for the integrator. Signal input is supplied through resistor 60 and transistor 68 to the summing junction at pin 2 of circuit 70. Diode 66 prevents the output of circuit 58 (pin 6) from going negative. Capacitor 43 is the critical integrating capacitor.

The pulse counter circuit 15 includes a large scale integrated circuit 72 containing an eight stage counter 74–75 and four gates 76, 77, 78 and 79. This is interfaced through diode 80, resistor 81, diode 82 and resistor 83 to provide a count, store, and reset function. The output is in straight binary digital format for use in controlling the multiplier circuit 16.

The multiplier circuit 16 includes resistors 85, 86, 87, 88, 89, 90 and 91; and integrated circuits 92, 93 and 94. Resistor 90 adjusts the circuit for zero output with zero input. A ladder network divider is formed by resistors 85 to 89, inclusive. Which of the resistors are in the divider at any given instant is a function of the solid state electronic switches 95, 96, 97, 98 and 99. The switches are in turn controlled as a function of the binary input from the countercircuit in integrated circuit 114. The output of the ladder network is buffered by circuit 94, which turns the total current that is supplied to the summing junction at pin 2 of circuit 94 to an inverted, amplified voltage output at pin 6 thereon. The analog input is supplied from circuit 70, pin 6. In conclusion, X times Y equals Z. X is the analog input; Y is the digital input; and Z appears at circuit 94, pin 6, which is the final multiplier output. Since the output signal is inverted, it may more correctly be called (−) Z.

The voltage to frequency convertor circuit includes resistors 100, 101, 102, 103, 104, 105, 106 and 107; capacitors 108, 109 and 110; diode 111, and integrated circuits 112 and 113. The circuit is constructed to be very stable and linear as the output frequency will represent the final computed output of the entire circuit.

The digital display module 18 is conventional, and need not be described in detail. As is known in the art, it is provided with an internal counter which is allowed to count up for a 100 millisecond at the end of a computational cycle. The output of the counter is used to drive a solid state numerical display, which indicates the final value of the computational measuring cycle to an operator.

The timing and sequence control circuit 19 provides a reset, convert, and display counter enable pulse in a predetermined succession. The components form a ten second timer 140, and a one hundred millisecond timer 141. During the time the operating switch 142 is closed, all circuits are reset and the 10 second timing capacitor 143 is discharged. Upon release of the switch, the reset voltage is released and the 10 second timer which includes integrated circuit 144 is activated. This produces a high output signal at pin 7. The trailing edge of the 10 second pulse triggers the 100 millisecond timer, thus supplying the counting aperture for the digital display module. The timer 140 includes capacitor 143, circuit 144, resistors 145, 146, 147, 148, 149, 150, 151 and 152; capacitors 153, 154 and 155; and transistors 156 and 157.

The timer 141 includes integrated circuit 160, resistors 161, 162 and 163; capacitors 164, 165 and 166.

Referring to FIG. 3 in the drawing, there are illustrated curves representing the various stages of operation of the device. The initial input curve is represented by reference character 169. This curve is directly inverted, as at 170, and a scale correction factor applied which vertically compresses the curve as indicated by reference character 171. The stabilized curve is indicated by reference character 172, wherein it will be observed that the curve now runs approximately parallel to a 0 baseline voltage. The digital output is indicated by reference character 173, the wave form integrator output by reference character 174, and the ten second timing aperture by reference character 175.

When a reading is ready to be made, the operator initiates a computational cycle by pressing a start button 176 on a control panel (not shown). All circuits are then reset. Next, the wave form integrator circuit and the pulse counter totalizer, 14 and 15, respectively, are brought into active states for a duration of 10 seconds. After this interval has passed, the convert command switches and leaves the above circuits holding the instantaneous final values which occurred at the end of the convert command cycle. The analog voltage at the output of the multiplier circuit 16 now represents the final computer data. This voltage causes the voltage to frequency convertor circuit 17 to output a specific frequency serial pulse train wave form. At this point, the binary coded decimal counters in circuit 18 are activated for a period of 100 milliseconds. At the end of this time, the binary coded decimal counters are halted, and the value remaining is displayed in circuit 18. The value represents the final computed numerical output.

I wish it to be understood that I do not consider the invention limited to the precise details of structure shown and set forth in this specification, for obvious modifications will occur to those skilled in the art to which the invention pertains.

I claim:

1. An improved physiological parameter analog computer for displaying components of measured pulsatile flow comprising: first means receiving a pulsatile wave form signal representing said flow; second frequency selection amplifier means passing frequency components of said signal above a predetermined frequency level; third means stabilizing signals received from said second means relative to a known baseline reference voltage; fourth means detecting each pulsatile impulse wave form from said third means and producing a single output pulse therefrom; fifth means providing a measured time interval; sixth means performing a voltage summation time derivative measurement during said time interval; seventh counter/means counting the number of pulsatile impulses occurring during said measured time interval; and eighth means multiplying the output of said seventh means by the output of said sixth means; and ninth means displaying the output of said eighth means.

2. A computer as set forth in claim 1, further comprising tenth means for selectively multiplying said pulsatile flow wave form signal by one of several electrical constants for obtaining scale factor correction.

3. A computer as set forth in claim 1 wherein said third means comprises a cutoff filter passing signal components above 0.3Hz.

* * * * *